US012366314B2

(12) United States Patent
Casura et al.

(10) Patent No.: US 12,366,314 B2
(45) Date of Patent: Jul. 22, 2025

(54) FLUID COUPLINGS

(71) Applicant: Colder Products Company, Roseville, MN (US)

(72) Inventors: Matthew G. Casura, St. Anthony, MN (US); Gary J. Harris, Maple Grove, MN (US); Andrew M. Quick, St. Paul, MN (US); Loi T. Truong, Savage, MN (US); Samuel J. Walker, Minneapolis, MN (US); Randall S. Williams, Minneapolis, MN (US)

(73) Assignee: Colder Products Company, Roseville, MN (US)

( * ) Notice: Subject to any disclaimer, the term of this patent is extended or adjusted under 35 U.S.C. 154(b) by 0 days.

(21) Appl. No.: 17/967,379

(22) Filed: Oct. 17, 2022

(65) Prior Publication Data
US 2023/0121701 A1 Apr. 20, 2023

Related U.S. Application Data

(60) Provisional application No. 63/344,209, filed on May 20, 2022, provisional application No. 63/256,957, filed on Oct. 18, 2021.

(51) Int. Cl.
*A61M 39/18* (2006.01)
*A61M 39/10* (2006.01)
(Continued)

(52) U.S. Cl.
CPC ........... *F16L 37/0841* (2013.01); *F16L 37/28* (2013.01); *F16L 2201/20* (2013.01)

(58) Field of Classification Search
CPC ....... F16L 2201/44; A61M 2039/1066; A61M 39/16; A61M 39/18
See application file for complete search history.

(56) References Cited

U.S. PATENT DOCUMENTS 3,865,411 A * 2/1975 Rowe .................... A61M 39/18
285/915
4,354,490 A * 10/1982 Rogers .................. A61M 39/16
604/905
(Continued)

FOREIGN PATENT DOCUMENTS

| CN | 109999333 | | 7/2019 | |
| FR | 2958365 A1 | * | 10/2011 | ............ A61M 39/18 |
| WO | WO 2020/124245 | | 7/2020 | |

OTHER PUBLICATIONS

International Search Report and Written Opinion in International Appln. No. PCT/US2022/046870, mailed on Feb. 3, 2023, 13 pages.
(Continued)

*Primary Examiner* — Matthew Troutman
*Assistant Examiner* — Fannie Kee
(74) *Attorney, Agent, or Firm* — Fish & Richardson P.C.

(57) ABSTRACT

Fluid handling couplings can include a main body with a front face and defining a longitudinal axis. Fluid handling couplings can include a post extending parallel to the longitudinal axis, and a post receptacle. Fluid handling couplings can include a seal coupled to the main body around the longitudinal axis. A portion of the seal can protrude from the front face of the main body. Fluid handling couplings can include a removable membrane releasably attached to the front face of the main body and covering the portion of the seal protruding from the front face of the main body. Fluid handling couplings can be genderless, can include manually openable valves, and can be configured for single-use aseptic fluid handling usage.

9 Claims, 18 Drawing Sheets

(51) Int. Cl.
 *F16L 37/084* (2006.01)
 *F16L 37/28* (2006.01)

(56) References Cited

U.S. PATENT DOCUMENTS

| | | | | |
|---|---|---|---|---|
| 7,121,556 | B2 * | 10/2006 | Barth | F16L 2201/44 |
| | | | | 277/649 |
| 8,439,838 | B2 * | 5/2013 | Mogensen | A61M 39/18 |
| | | | | 600/365 |
| 9,726,308 | B2 * | 8/2017 | Williams | A61M 39/18 |
| 2002/0148514 | A1 | 10/2002 | Taneya et al. | |
| 2003/0030272 | A1 * | 2/2003 | Johnson | A61M 39/18 |
| | | | | 285/70 |
| 2005/0016620 | A1 | 1/2005 | Proulx et al. | |
| 2008/0217915 | A1 | 9/2008 | Arthun et al. | |
| 2008/0277878 | A1 * | 11/2008 | Arthun | A61M 39/18 |
| | | | | 285/70 |
| 2010/0230950 | A1 * | 9/2010 | Williams | A61M 39/18 |
| | | | | 285/38 |
| 2013/0289517 | A1 | 10/2013 | Williams et al. | |
| 2015/0028586 | A1 | 1/2015 | Gerst et al. | |
| 2016/0053927 | A1 | 2/2016 | Whitaker | |
| 2017/0284584 | A1 * | 10/2017 | Kesselaar | A61M 39/18 |
| 2018/0304061 | A1 | 10/2018 | Sautereau | |
| 2021/0062946 | A1 | 3/2021 | Gerst et al. | |

OTHER PUBLICATIONS

Extended European Search Report in European Appln No. 22884313.2, dated Dec. 17, 2024, 12 pages.
Extended European Search Report in European Appln No. 22884313.2, dated Mar. 10, 2025, 10 pages.

\* cited by examiner

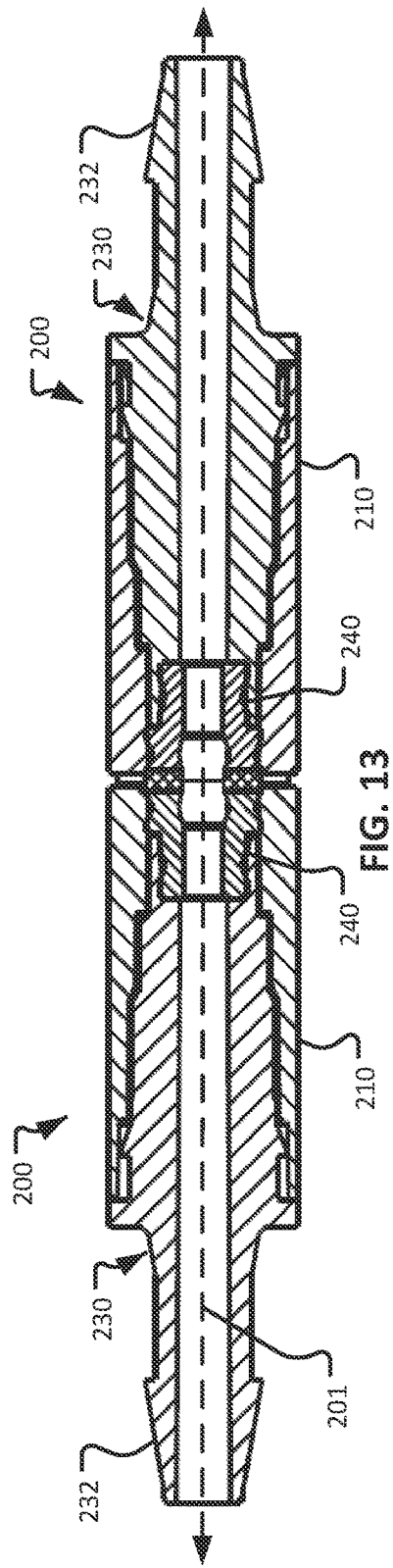
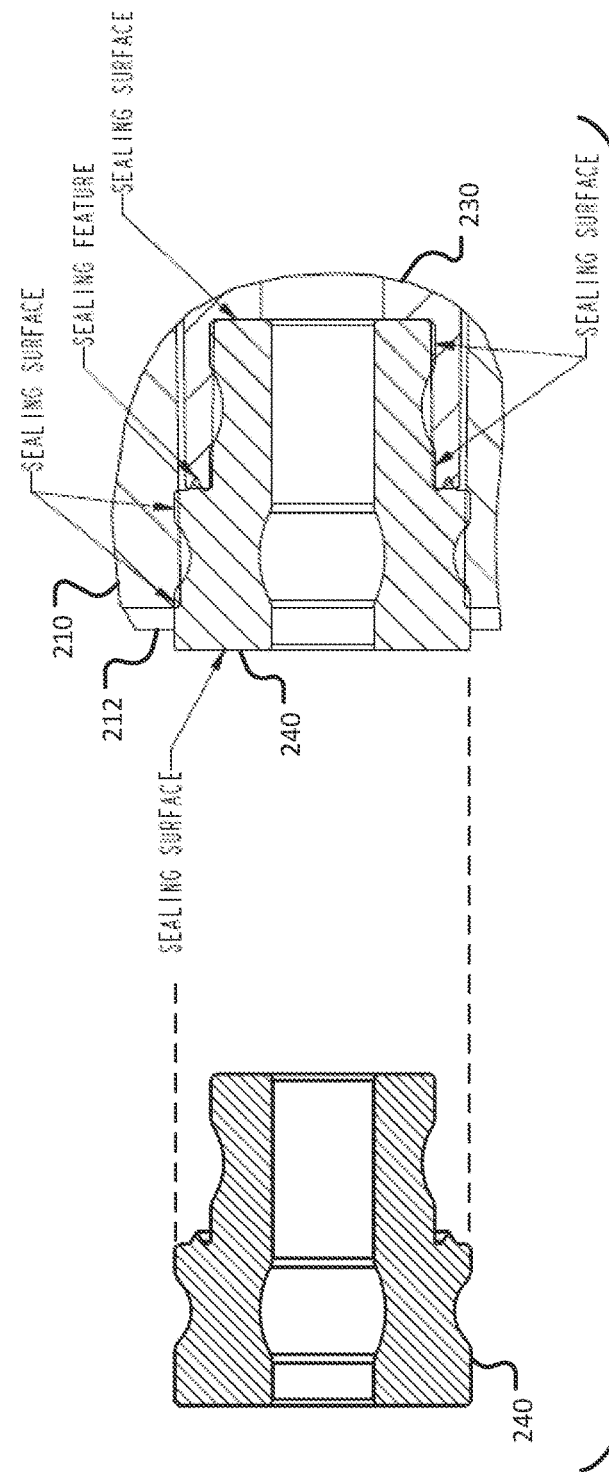
FIG. 13
FIG. 14

FLUID COUPLINGS

CROSS-REFERENCE TO RELATED APPLICATIONS

This application claims the benefit of U.S. Provisional Application Ser. No. 63/256,957, filed Oct. 18, 2021, and U.S. Provisional Application Ser. No. 63/344,209, filed May 20, 2022. The disclosure of the prior application is considered part of (and is incorporated by reference in) the disclosure of this application.

BACKGROUND

1. Technical Field

This document relates to fluid handling couplings.

2. Background Information

Fluid handling components such as fluid couplings allow fluid communication between two or more components. Some fluid couplings include features that allow male and female components (or two genderless fluid couplings) to be quickly connected, and may include one or more internal valve components that selectively block or allow flow of fluid through the coupling.

SUMMARY

This document describes a number of fluid coupling devices for fluid systems and methods. In some embodiments, the fluid coupling devices can be implemented as single-use, aseptic fluid coupling connection devices. In the context of this disclosure, the term "fluid" means any substance that can be made to flow including, but is not limited to, liquids, gases, granular or powdered solids, mixtures or emulsions of two or more fluids, suspensions of solids within liquids or gases, gels, vapors, steam, mists, etc., without limitation.

In one aspect, this disclosure is directed to a fluid coupling device that includes a main body defining a longitudinal axis. The main body has a front face. The fluid coupling device also includes a post extending parallel to the longitudinal axis, and a post receptacle. The fluid coupling device also includes a seal coupled to the main body around the longitudinal axis. A portion of the seal protrudes from the front face of the main body. The fluid coupling device also includes a removable membrane releasably attached to the front face of the main body and covering the portion of the seal protruding from the front face of the main body. The fluid coupling device also includes a protective cover releasably engaged with the post and post receptacle of the main body. Two layers of the removable membrane are captured between the protective cover and the front face of the main body.

Such a fluid coupling device may optionally include one or more of the following features. The seal may have a circular projection that has a triangular cross-sectional shape. The circular projection may extend parallel to the longitudinal axis. The seal may include two annular concavities defined by the outer surface of the seal. The seal may include a portion having an hourglass cross-sectional shape. The fluid coupling may be genderless such that two of the fluid coupling devices can be coupled to each other. The protective cover may include a pull ring. The pull ring may define an opening configured to receive a finger. The protective cover may include a membrane receiver portion that holds and protects a portion of the removable membrane.

In another aspect, this disclosure is directed to a fluid coupling device that includes a main body that defines a longitudinal axis and includes a front face, a post extending parallel to the longitudinal axis, and a post receptacle. The fluid coupling device also includes a seal coupled to the main body around the longitudinal axis. A portion of the seal protrudes from the front face of the main body. The fluid coupling device also includes a lever valve movably coupled to the main body. The lever valve is reconfigurable between a first position in which the lever valve is engaged with the seal and a second position in which the lever valve is spaced apart from the seal. The fluid coupling device also includes a removable membrane releasably attached to the front face of the main body and covering the portion of the seal protruding from the front face of the main body.

Such a fluid coupling device may optionally include one or more of the following features. The fluid coupling device may also include a protective cover releasably engaged with the post and post receptacle of the main body. In some embodiments, two layers of the removable membrane are captured between the protective cover and the front face of the main body. The lever valve may be pivotable relative to the main body about the longitudinal axis to reconfigure the lever valve between the first and second positions. In some embodiments, pivoting the lever valve causes translation of the lever valve along the longitudinal axis between the first and second positions. The seal may include a portion having an hourglass cross-sectional shape. The fluid coupling device may be genderless such that two of the fluid coupling devices can be coupled to each other. In some embodiments, protective cover includes a pull ring. The pull ring may define an opening configured to receive a finger. In some embodiments, the protective cover includes a membrane receiver portion that holds and protects a portion of the removable membrane.

In particular embodiments, the fluid coupling devices described herein are single-use devices because, after the two portions of the coupling (also referred to herein as "coupling halves" and/or "connectors") are connected to each other, the coupled portions are designed to resist uncoupling. For example, such single-use coupling devices are equipped with one or more mechanical components that operate like locks to maintain the two portions of the coupling in the coupled state. Hence, in these particular embodiments, the fluid coupling devices provided herein are structurally configured to be single-use connection devices so that, after the single-use coupling halves have been connected to each other, they cannot be operably disconnected from each other (as such, preserving the sterility or biological integrity of the system/flow path/etc.).

Additionally, in such single-use embodiments or in other embodiments, the fluid coupling devices can be configured as "aseptic" coupling devices in that they can be connected to each other while inhibiting biological contamination from migrating into the flow paths. Such an "aseptic" coupling will also serve to limit the exposure of the fluid to the surrounding environment.

Further, in such single-use embodiments, or other embodiments, the fluid coupling devices can be configured as genderless couplings. That is, the two coupling portions can be designed exactly alike (or substantially alike) so that there is no male or female coupling halves as in many conventional fluid coupling designs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 13 is a longitudinal cross-sectional view of the two fluid couplings in the coupled configuration as shown in FIG. 12.

FIG. 14 is a cutaway cross-section view showing a seal of the fluid couplings of FIG. 9 or 10.

Like reference numbers represent corresponding parts throughout.

DETAILED DESCRIPTION

This document describes fluid handling couplings. For example, this document describes fluid handling couplings that are genderless, that optionally include manually openable valves, and that are configured for single-use aseptic fluid handling usage contexts.

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies. As used herein, the term "aseptic" refers to any process that maintains a sterilized surface or volume.

Figure 2:
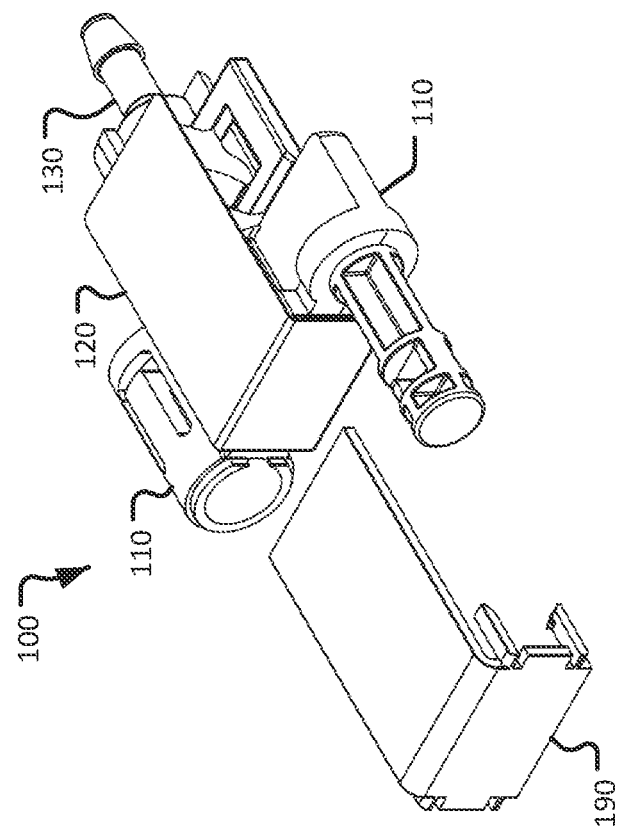
FIG. 2 is another perspective view of the fluid coupling of FIG. 1 with the protective cap separated.
Figure 1:
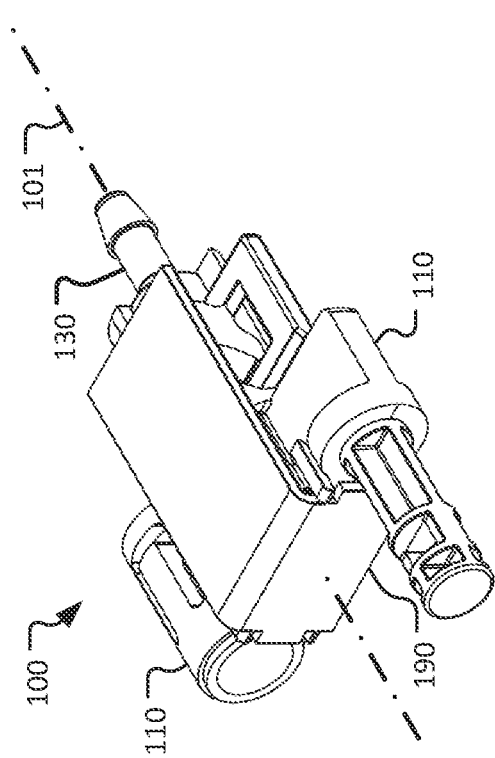
FIG. 1 is a perspective view of an example fluid coupling in accordance with some embodiments provided herein.

FIG. 1 shows a fluid coupling device 100 that includes a protective cover 190 engaged with the main body 110 of the fluid coupling device 100. The fluid coupling device 100 defines a longitudinal axis 101. The protective cover 190 is manually removable, and can be separated from the main body 110 as illustrated in FIG. 2. The protective cover 190 provides protection to a removable membrane member 120 that is adhered (e.g., heat welded/sealed, ultrasonic welded, adhered using an adhesive, etc.) to the front face of the main body 110. In some embodiments, the removable membrane member 120 is made of a porous material that allows the passage of gaseous materials (e.g., for sterilization) while preventing the passage of larger materials such as biological contaminants and/or particulate matter. In some embodiments, the removable membrane member 120 (and other removable membrane members described herein) is made of a foil or other suitable flexible materials. The removable membrane member 120 can provide a sterile barrier to prevent contamination of the inner fluid-contacting surfaces of the main body 110. In some embodiments, the fluid coupling 100 can be provided to end users in a sterile condition, or in a condition ready for sterilization.

The materials from which one or more of the components of the fluid coupling device 100 (and other fluid couplings described herein) can be made include thermoplastics. In particular embodiments, the materials from which the components of the fluid coupling device 100 are made of are thermoplastics, such as, but not limited to, acetal, polycarbonate, polysulfone, polyether ether ketone, polysulphide, polyester, polyvinylidene fluoride (PVDF), polyethylene, polyphenylsulfone (PPSU; e.g., Radel®), acrylonitrile butadiene styrene (ABS), polyetherimide (PEI; e.g., Ultem®), polypropylene, polyphenylene, polyaryletherketone, and the like, and combinations thereof. In some embodiments, the thermoplastics can include one or more fillers such as, but not limited to, glass fiber, glass bead, carbon fiber, talc, etc.

In some embodiments, the materials from which one or more of the components of the fluid coupling device 100 are made of include metals such as, but not limited to copper, stainless steel, brass, aluminum, plated steel, zinc alloys, and the like. In particular embodiments, the fluid coupling device 100 is metallic-free.

In some embodiments, as described further below, the fluid coupling device 100 can include one or more seal members. In some embodiments, the seal members of the fluid coupling device 100 (and the other fluid couplings described herein) can comprise materials such as, but not limited to, silicone, fluoroelastomers (FKM), ethylene propylene diene monomer (EPDM), thermoplastic elastomers (TPE), buna, buna-N, thermoplastic vulcanizates (TPV), and the like. The cross-sectional shape of such seal members can be circular, D-shaped, X-shaped, hourglass shaped, square, rectangular, U-shaped, multi-lobed, L-shaped, V-shaped, and the like, or any other suitable shape, without limitation.

Figure 3:
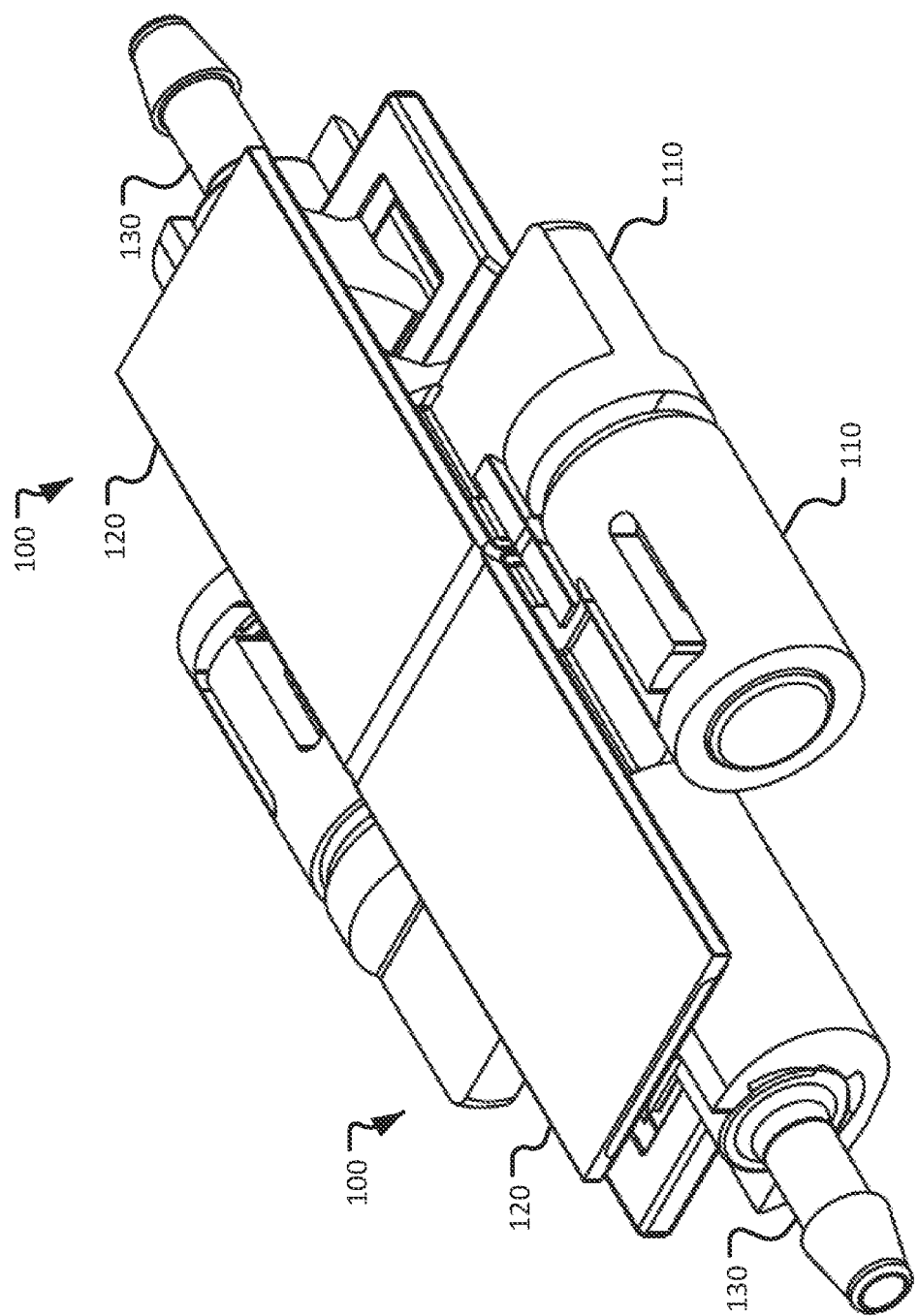
FIGS. 3 and 4 are perspective views of two of the fluid couplings of FIG. 1 in a first coupled arrangement.
Figure 4:
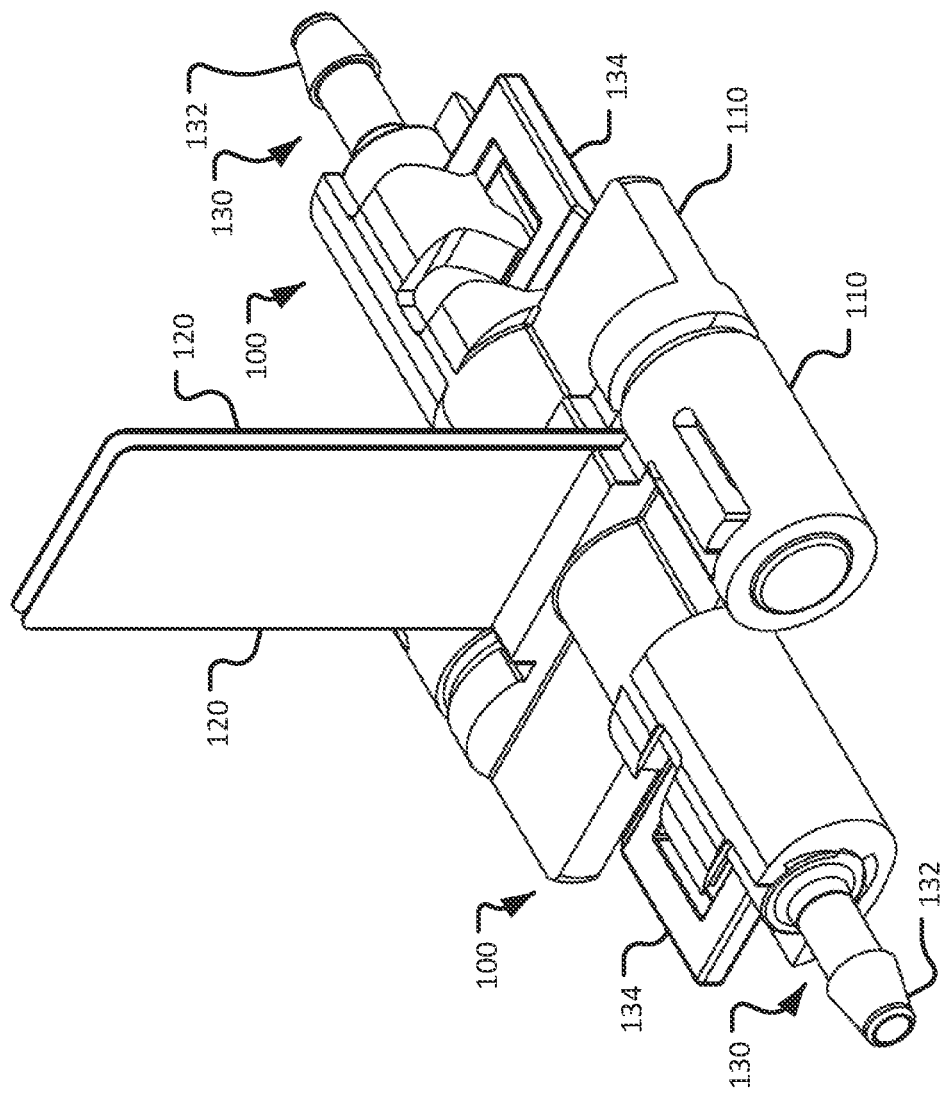

FIGS. 3 and 4 show two of the fluid coupling devices 100 in a coupled arrangement with the removable membrane members 120 still attached to the main bodies 110. In this embodiment, the fluid coupling device 100 (and the other fluid couplings described herein) is genderless (meaning that two of the fluid coupling devices 100 can be coupled to each other, and that there are no 'male' and 'female' coupling devices). In this configuration, the main bodies 110 are latched together, but the membranes 120 are still attached to the respective front faces of the main bodies 110. In this arrangement, there is a light compression between the membranes 120. As shown in FIG. 4, the free ends (tail ends) of the membranes 120 can be positioned to overlap each other in preparation for removal of the membranes 120.

In FIG. 4, it can be seen that the fluid coupling devices 100 include termination members 130. The termination member 130 includes a termination 132, a lever 134, and a valve member 136 (e.g., visible in FIGS. 6 and 8). The termination member 130 is movably coupled to the main body 110. While in the depicted configuration the termination 132 is a hose barb, any other suitable type of termination can be used such as, but not limited to, a compression fitting, a quick disconnect, a sanitary fitting, hydraulic quick connection, luer fitting, a solder connection, a welded connection, a threaded connection (e.g., straight thread or pipe thread), and so on, without limitation. Such connections can be straight (as depicted) or in another arrangement such as, but not limited to, a 90° elbow arrangement, a 45° elbow, a straight fitting, a Tee fitting, a Y-fitting, and so on. In some embodiments, the fluid coupling devices 100 can be configured to be fluidly coupled with a fluid conduit such as, but not limited to, a tube, pipe, a manifold, and the like, without limitation. In some embodiments, fluid coupling devices 100 can be configured to be fluidly coupled with a bag or other type of container.

Figure 5:
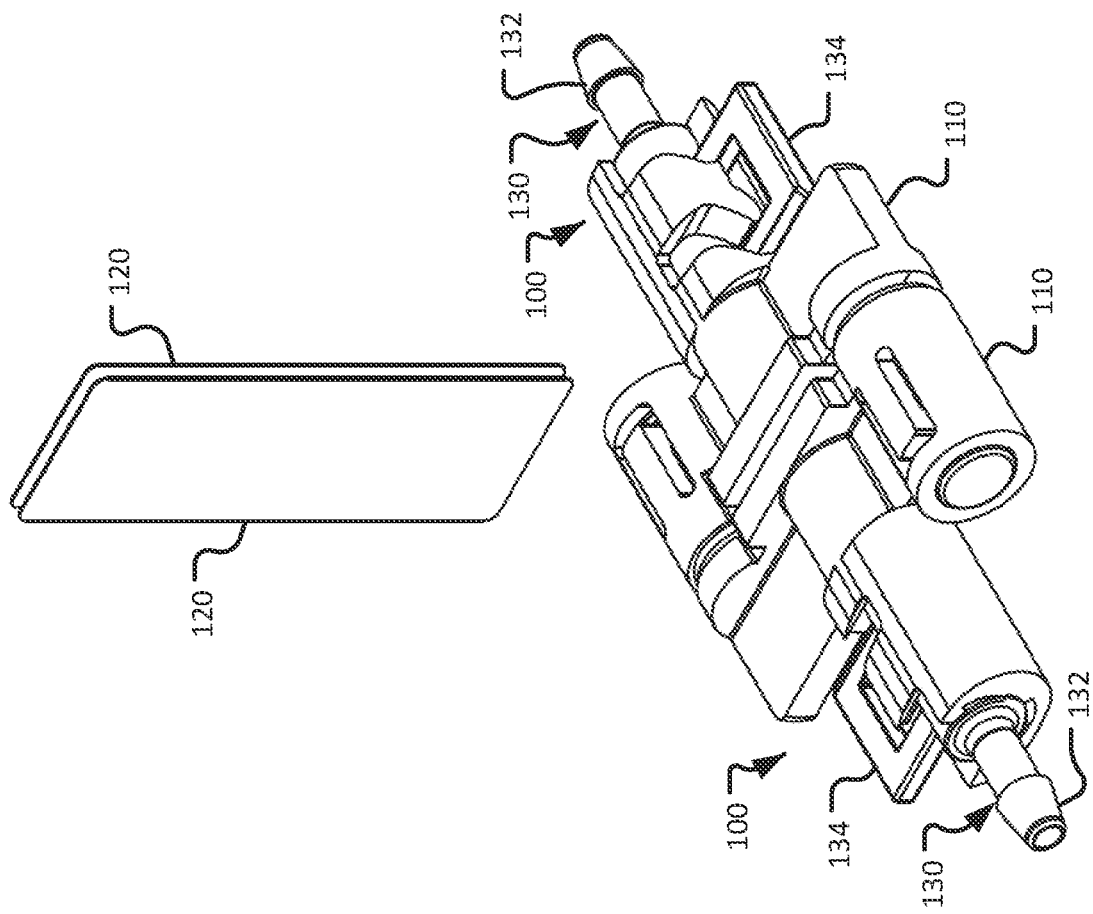
FIG. 5 is a perspective view of two of the fluid couplings of FIG. 4 in a second coupled arrangement.

FIG. 5 shows the membranes 120 removed from the main bodies 110. This removal can be performed by a user who manually pulls the membranes 120 transversely away from the main bodies 110. In some embodiments, the membranes 120 are folded and the folds can roll/progress when the membranes 120 are pulled so as to peel the membranes 120 off or the front faces of the main bodies 110.

Figure 6:
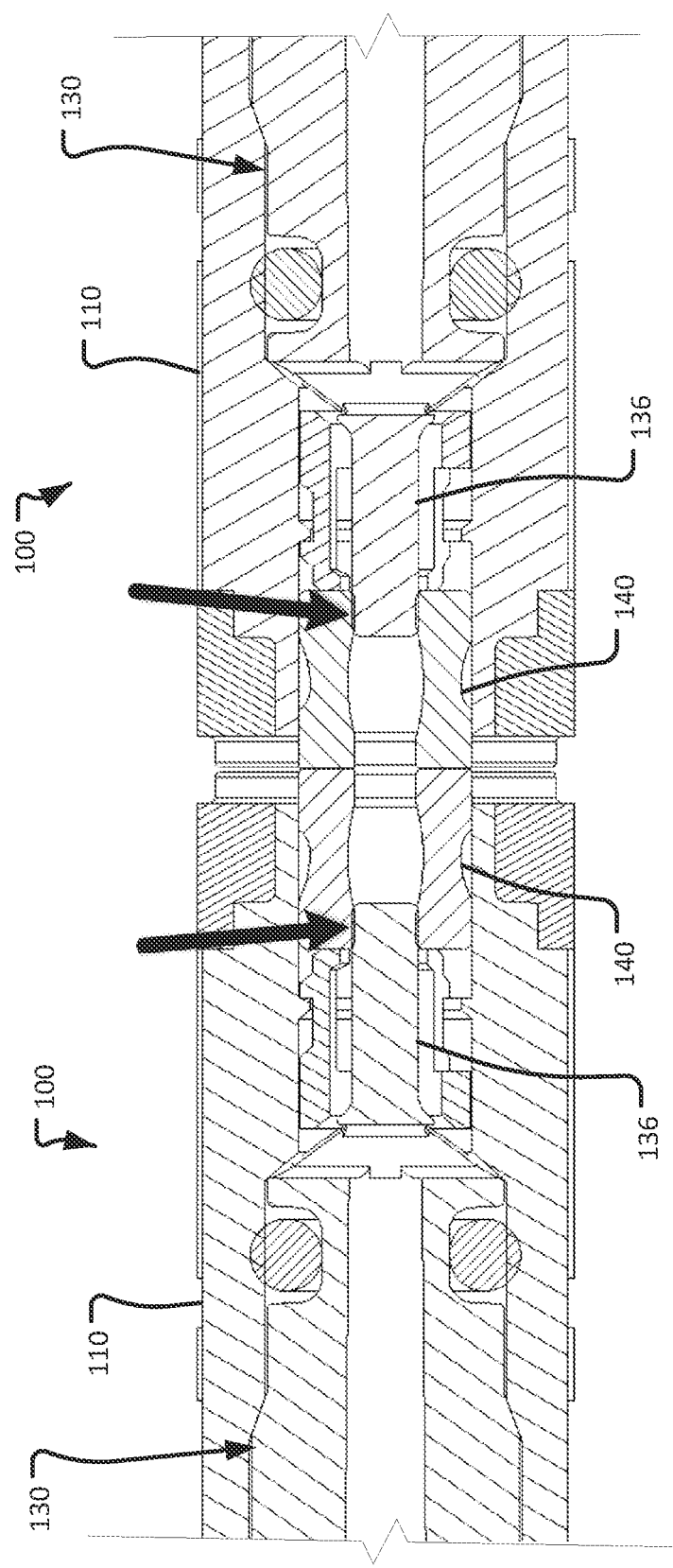
FIG. 6 is a partial cross-sectional view of the two fluid couplings of FIG. 5.

FIG. 6 shows a longitudinal cross-section view of the front-end portions of the two couplings 100 after removal of the membranes 120 (as in FIG. 5). It can be seen that each of the couplings 100 includes a seal 140 coupled with the main body 110 and slightly protruding from the front face of the main body 110. The two seals 140 are in contact with each other (after the membranes 120 are removed). Accordingly, because of the sealing between the two seals 140, the inner fluid contacting surfaces of the main bodies 110 are still prevented from being contaminated.

It can also be seen that the seals 140 at the front faces of the main bodies 110 are each plugged by a valve member 136 in this configuration. The valve member 136 is at an end of the termination member 130. The valve members 136 extend into the inner diameter of the seals 140 to block fluid flow through the couplings 100. Accordingly, no fluid flow path is opened through the fluid couplings 100 in this configuration.

Figure 7:
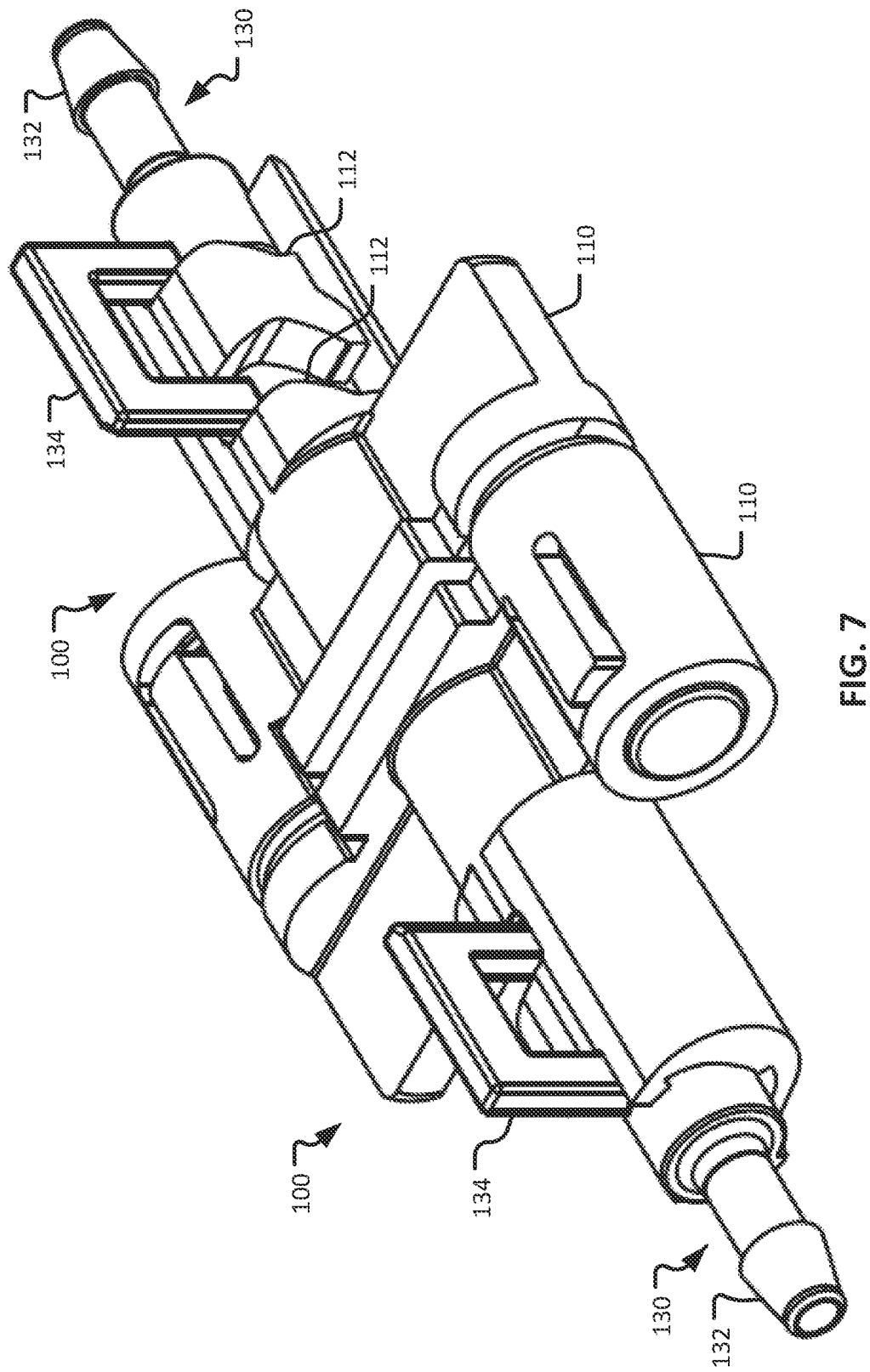
FIG. 7 is a perspective view of two of the fluid couplings of FIG. 5 in a third coupled arrangement.

FIG. 7 shows the fluid couplings 100 in yet another coupled configuration. In this configuration, the levers 134 of the termination members 130 have been manually rotated or pivoted in relation to the main bodies 110 (as compared to the configuration of FIG. 5). Rotation of the termination members 130 via the levers 134 causes the termination members 130 to not only rotate in relation to the main bodies 110, but also to translate longitudinally in relation to the main bodies 110. That is the case because the arms of the levers 134 run along angled cam surfaces 112 defined by the main bodies 110 that drive the termination members 130 axially away from the front faces of the main bodies 110.

Figure 8:
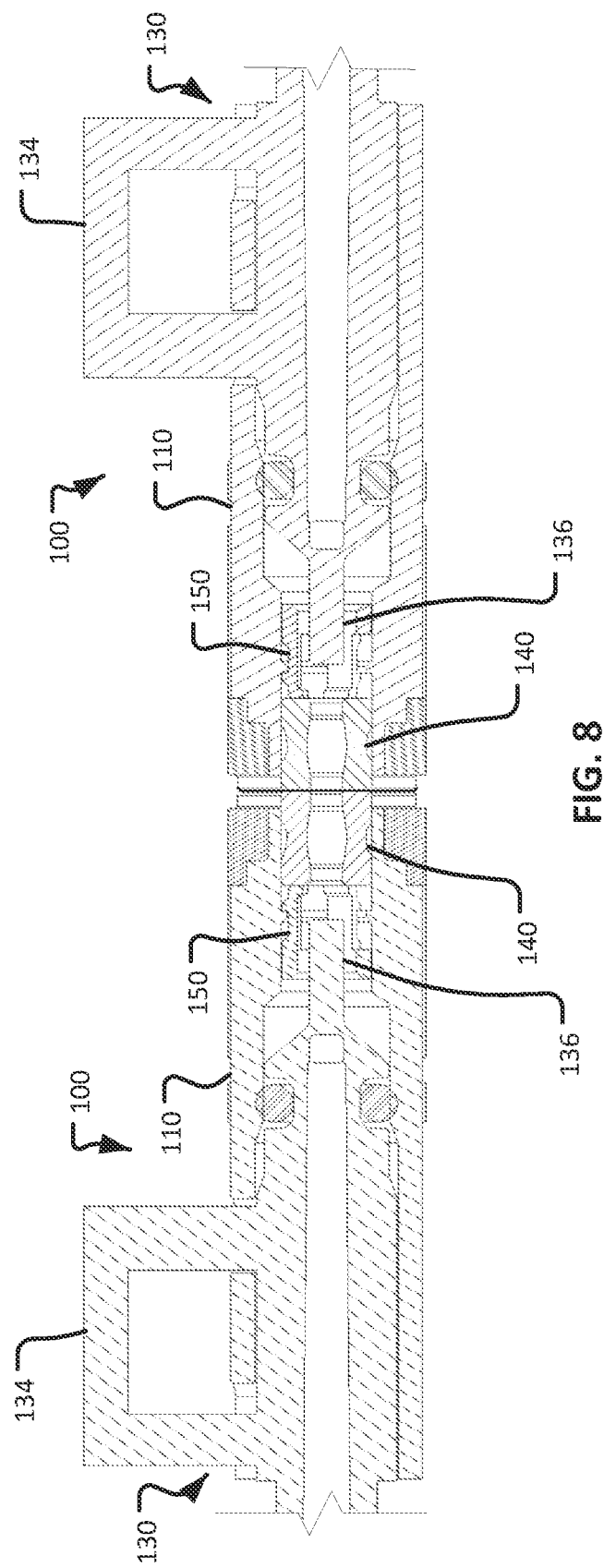
FIG. 8 is a partial cross-sectional view of the two fluid couplings of FIG. 7.

FIG. 8 shows a longitudinal cross-section view of the front-end portions of the two couplings 100 after the levers 134 of the termination members 130 have been rotated or pivoted (as in FIG. 7). It can be seen that the seals 140 at the front faces of the main bodies 110 are each no longer plugged by the valve members 136 in this configuration because the termination members 130 have axially translated away from the front faces of the main bodies 110 when the levers 134 were rotated. Accordingly, a fluid flow path is opened through the two joined fluid couplings 100 in this configuration. The fluid flow path is an aseptic fluid flow path.

FIG. 8 also shows an optional retainer 150 between the seals 140 and the valve members 136. This retainer 150 is not required in all embodiments. The retainer 150, when included, can be advantageous especially during assembly of the fluid couplings 100. That is, after the removable membrane 120 is adhered to the front face of the main body 110, then the retainer 150 can be pushed forward to push the seal 140 forward and into contact with the membrane 120. By waiting until after the membrane 120 is adhered to the front face prior to pushing the seal 140 forward, the membrane 120 does not have the stresses from the seal 140 when the adhesion process is being performed. Therefore, the attachment of the membrane 120 is unencumbered by the seal 140 (which extends slightly beyond the front face of the main body 110).

Figure 9:
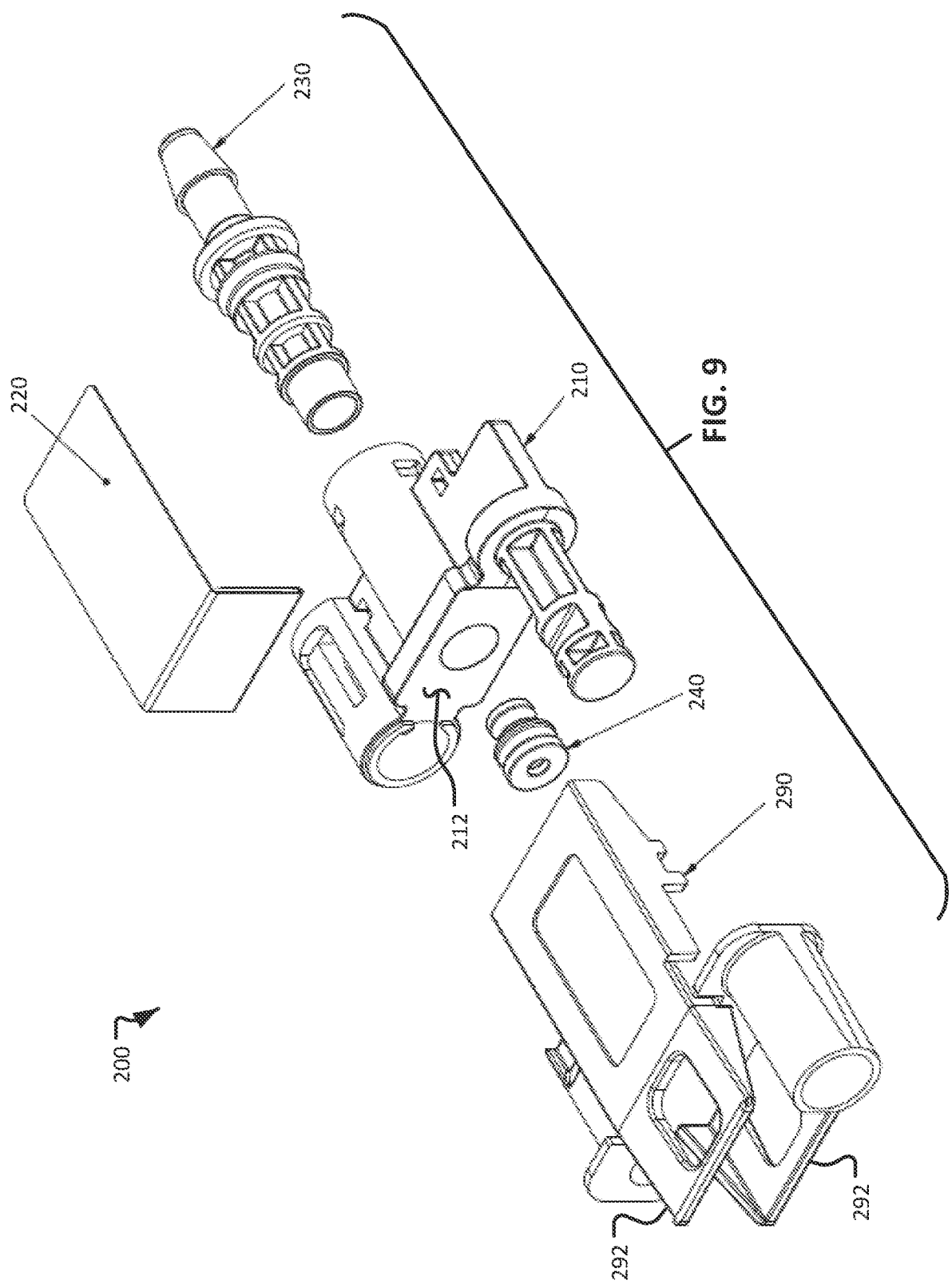
FIG. 9 is an exploded perspective view of another example fluid coupling in accordance with some embodiments provided herein.

FIG. 9 shows another example fluid coupling device 200. The fluid coupling device 200 is functionally/operationally similar to the fluid coupling device 100, except that the fluid coupling device 200 does not include a valve like the fluid coupling device 100 does.

The fluid coupling device 200 includes a main body 210, a removable membrane 220, a termination member 230, a seal 240, and a protective cover 290. The termination member 230 and the seal 240 are fixedly coupled with the main body 210. The seal 240 is coupled to the main body 210 and a portion of the seal 240 protrudes from the front face of the main body 210. The removable membrane 220 and the protective cover 290 are removably coupled with the main body 210.

In the depicted embodiment, the seal 240 is assembled into the main body 210 from the front face 212 of the main body 210. In contrast, the termination member 230 is assembled into the main body 210 from the end of the main body 210 that is opposite of the front face 212. In some embodiments, the termination member 230 snaps into engagement with the main body 210. The action of snapping the termination member 230 into engagement with the main body 210 can advantageously be accompanied by audible and tactile feedback. In some embodiments, the termination member 230 is rotatable in relation to the main body 210. In some embodiments, the termination member 230 is not rotatable in relation to the main body 210.

Figure 10:
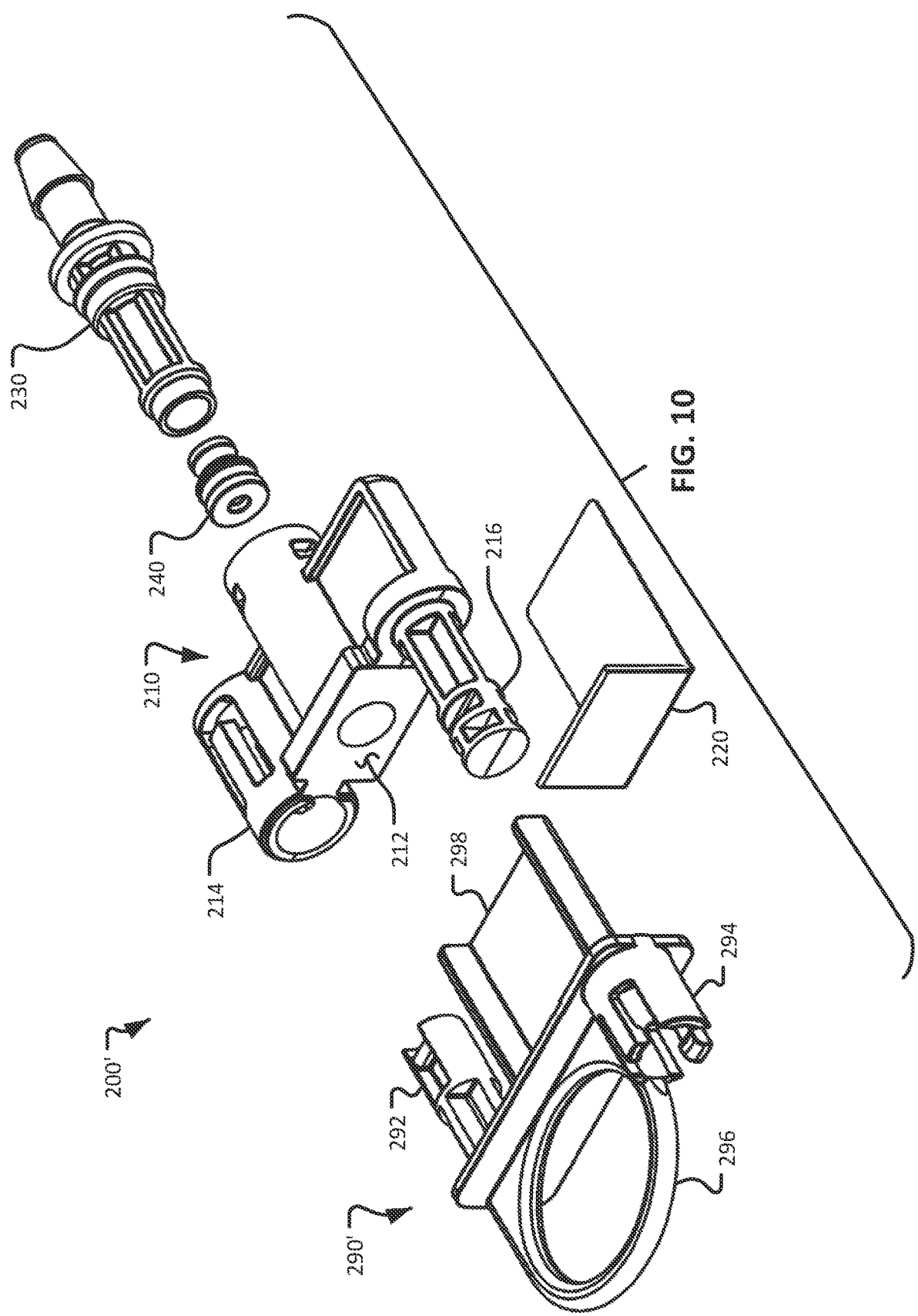
FIG. 10 is an exploded perspective view of a variation of the fluid coupling of FIG. 9.

FIG. 10 shows an example device 200' which is a variation of the fluid coupling device 200. The fluid coupling device 200' is different than the fluid coupling device 200 in that it includes a different style of protective cover 290'. The protective cover 290' includes a post 292, a post receptacle 294, a pull ring 296, and a membrane receiver 298. The post 292 releasably couples with a post receptacle 214 of the main body 210. The post receptacle 294 releasably couples with a post 216 of the main body 210. The membrane receiver 298 holds and protects a portion of the removable membrane 220 while the protective cover 290' is engaged with the main body 210.

In preparation for use (i.e., in preparation for coupling two of the fluid coupling devices 200/200' together in an operable configuration), the protective cover 290/290' is removed from the main body 210. This can be accomplished by manually pinching the handles 292 toward each other and then pulling the protective cover 290 away from the main body 210 to disengage the two from each other. In the alternative device 200' the protective cover 290' is simply pulled away from the main body 210 using the pull ring 296.

With the protective covers 290/290' of two of the fluid coupling devices 200/200' removed, the two fluid coupling devices 200/200' can then be engaged to each other (with the membranes 220 being pushed against each other between the front faces of the main bodies 210). The two fluid coupling devices 200/200' will snap together and latch to each other. The action of snapping two fluid coupling devices 200 can advantageously be accompanied by audible and tactile feedback.

Figure 11:
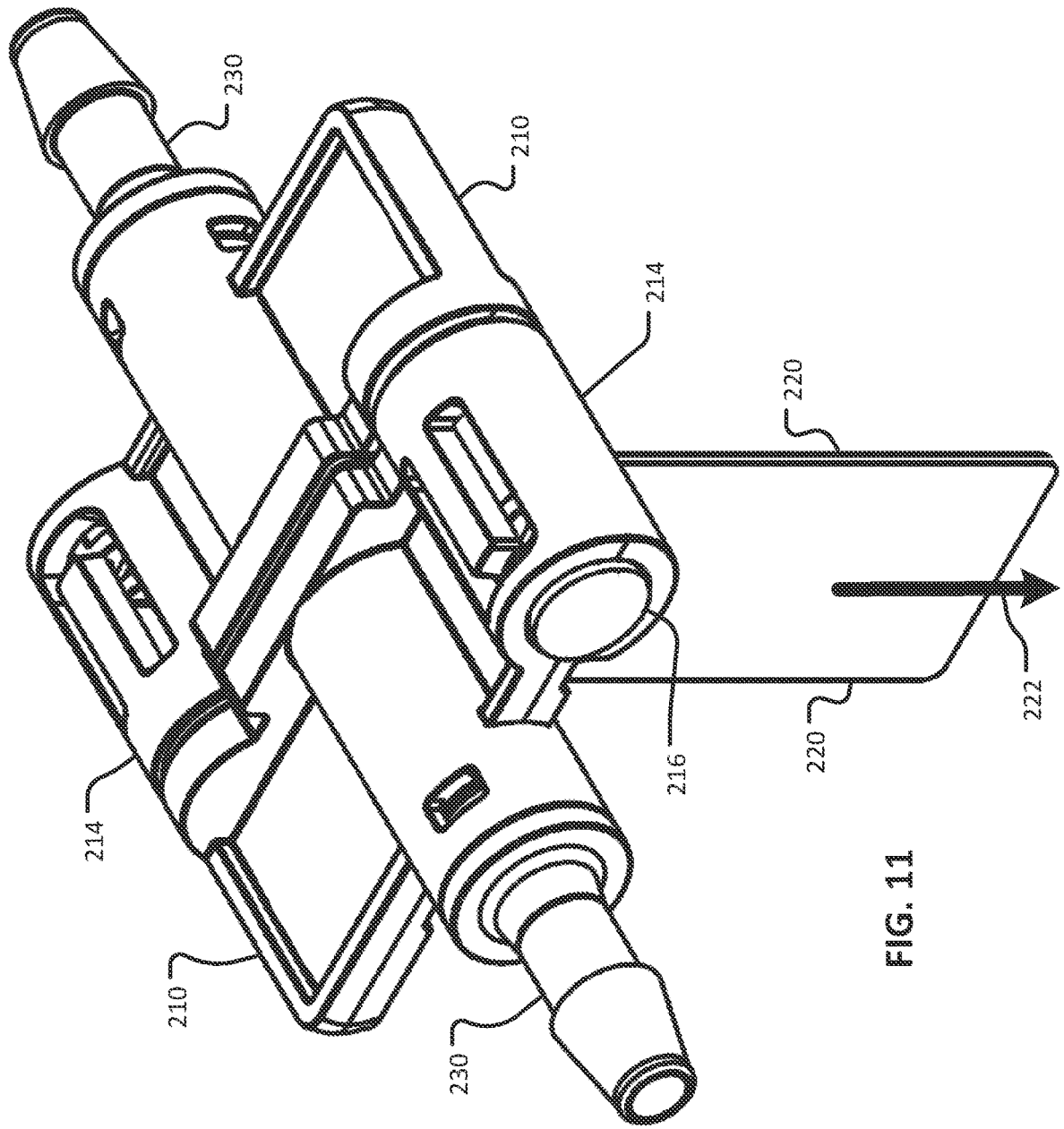
FIG. 11 is a perspective view of two of the fluid couplings of FIG. 9 or 10 in a pre-coupled configuration.

FIG. 11 shows two of the fluid coupling devices 200/200' (with protective covers 290/290' removed) in a pre-coupled configuration. In the pre-coupled configuration, the removable membranes 220 are pressed against each other between the seals 240. The main bodies 210 are latched together because the post 292 of the first fluid coupling device 200/200' is coupled with the post receptacle 294 of the second fluid coupling device 200/200', and the post 292 of the second fluid coupling device 200/200' is coupled with the post receptacle 294 of the first fluid coupling device 200/200'. The coupling between the two fluid coupling devices 200/200' compresses the removable membranes 220 between the seals 240. There are actually four (4) layers of the removable membranes 220 between the seals 240.

The removable membranes 220 can be stripped away by simply pulling them away from the main bodies 210 as indicated by the arrow 222. The folds of the removable membranes 220 roll along the front faces 212 as the removable membranes 220 are pulled away.

Figure 12:
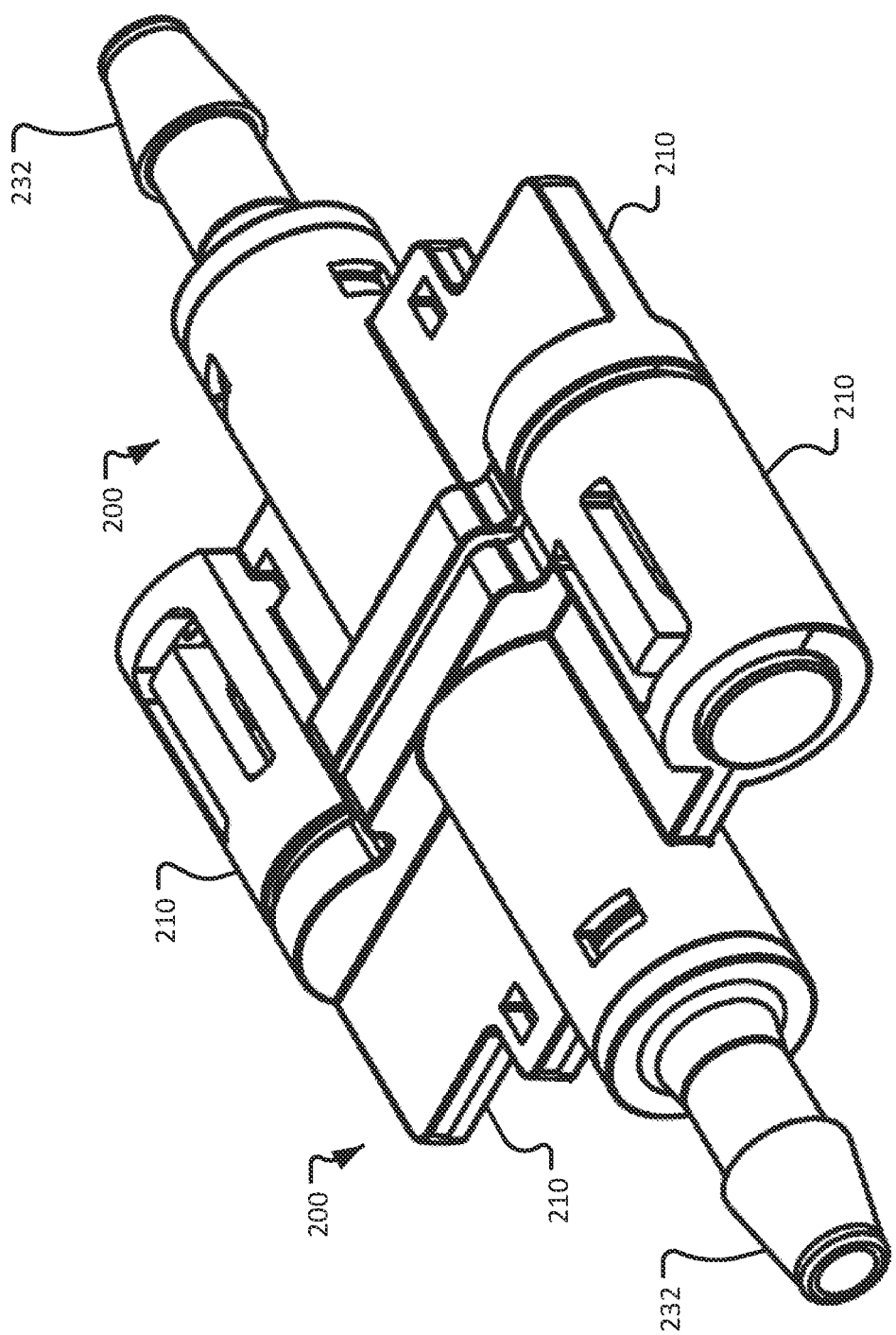
FIG. 12 is a perspective view of two of the fluid couplings of FIG. 9 or 10 in an operationally coupled configuration.

With the two fluid coupling devices 200/200' latched together, the membranes 220 are then removed. This results in the operative configuration shown in FIG. 12. An open fluid flow path is created between the terminations 232. The open fluid flow path 201 is shown in FIG. 13.

FIG. 14 shows the seal 240 in its static position relative to the main body 210. It can be seen that the seal 240 protrudes slightly beyond the front face 212 of the main body. This protrusion of the seal 240 ensures that there is a slight compression fit between two seals 240 when two fluid coupling devices 200 latched together.

The seal 240 has multiple sealing features. The seal 240 seals against the main body 210 in two places. The seal 240 seals against the termination member 230 in four places (as indicated in FIG. 14). For example, the face of the termination member 230 seals against a circular projection of the seal 240 that has a triangular cross-section in this embodiment. In total, the seal 240 has seven (7) sealing areas/features (as indicated in FIG. 14). The largest portion of the seal 240 has an hourglass cross-sectional shape (with an outer-facing annular recess and a corresponding inner-facing annular recess). This shape helps allow the seal 240 to compress longitudinally when two seals 240 are pressed against each other (when two of the fluid coupling devices 200 are coupled together).

Figure 15:
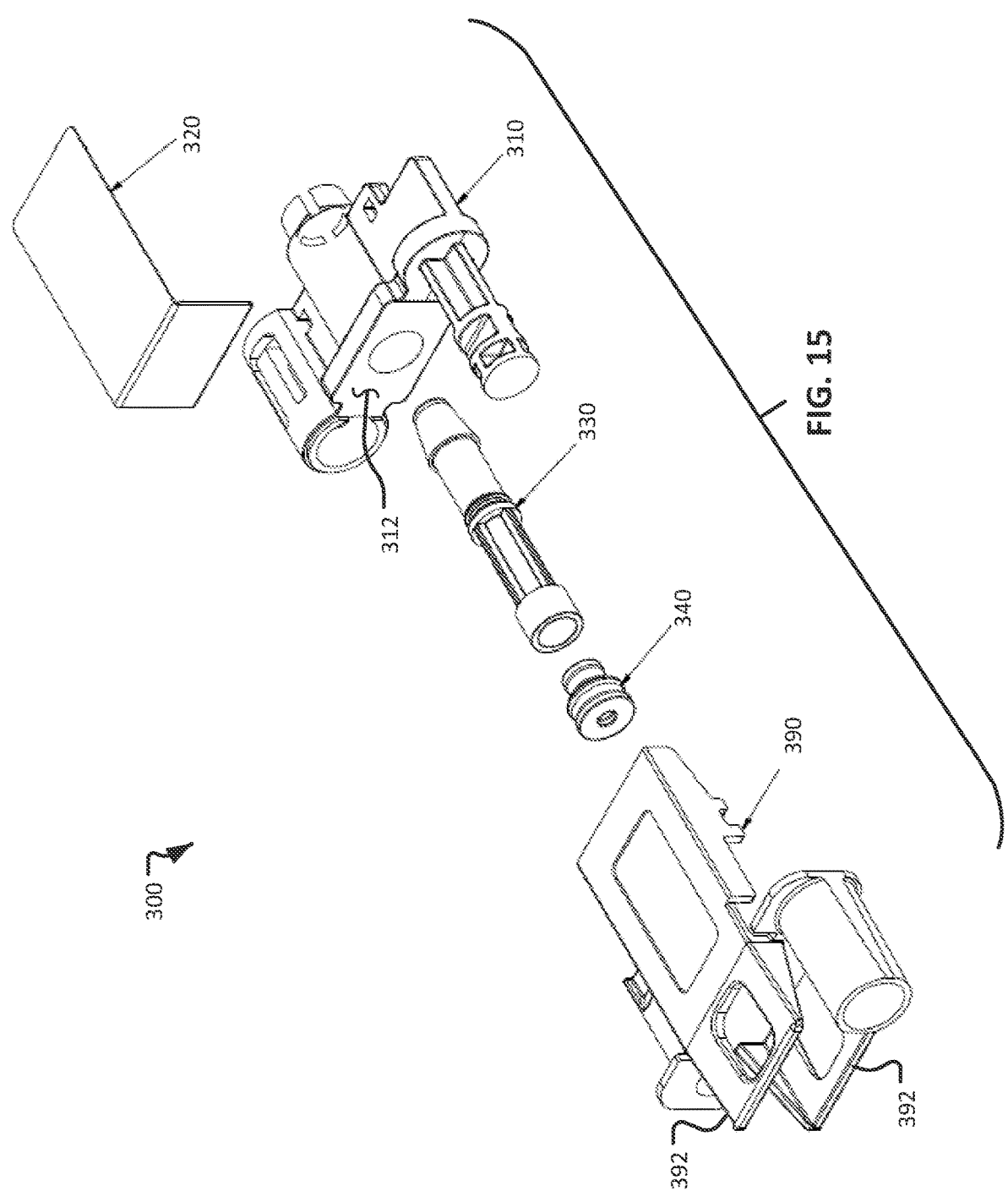
FIG. 15 is an exploded perspective view of another example fluid coupling in accordance with some embodiments provided herein.

FIG. 15 shows another example fluid coupling device 300. The fluid coupling device 300 is functionally/operationally similar to the fluid coupling device 100, except that the fluid coupling device 300 does not include a valve like the fluid coupling device 100 does.

The fluid coupling device 300 includes a main body 310, a removable membrane 320, a termination member 330, a seal 340, and a protective cover 390. The termination member 330 and the seal 340 are fixedly coupled with the main body 310. The removable membrane 320 and the protective cover 390 are removably coupled with the main body 310.

In the depicted embodiment, the seal 340 is assembled into the main body 310 from the front face 312 of the main body 310. Similarly, the termination member 330 is also assembled into the main body 310 from the front face 312 of the main body 310. The termination member 330 is installed first, and the seal 340 is installed thereafter. In some embodiments, the termination member 330 snaps into engagement with the main body 310. Alternatively, in some embodiments the termination member 330 can be joined to the main body 310 using ultrasonic welding, adhesive, and other suitable joining techniques. In some embodiments, the termination member 330 is rotatable in relation to the main body 310. In some embodiments, the termination member 330 is not rotatable in relation to the main body 310.

In preparation for use (i.e., in preparation for coupling two of the fluid coupling devices 300 together in an operable configuration), the protective cover 390 is removed from the main body 310. This can be accomplished by manually pinching the handles 392 toward each other and then pulling the protective cover 390 away from the main body 310 to disengage the two from each other.

With the protective covers 390 of two of the fluid coupling devices 300 removed, the two fluid coupling devices 300 can then be engaged to each other (with the membranes 320 being pushed against each other between the front faces of the main bodies 310). The two fluid coupling devices 300 will snap together and latch to each other. The action of snapping two fluid coupling devices 300 can advantageously be accompanied by audible and tactile feedback. Each fluid coupling device 300 includes a post and a post receptacle. To couple two fluid coupling devices 300 together (e.g., to snap them into engagement with each other), the post of a first fluid coupling device 300 is inserted in the post receptacle of a second fluid coupling device 300, and the post of a second fluid coupling device 300 is inserted in the post receptacle of a first fluid coupling device 300. The posts latch inside of the post receptacles.

Figure 16:
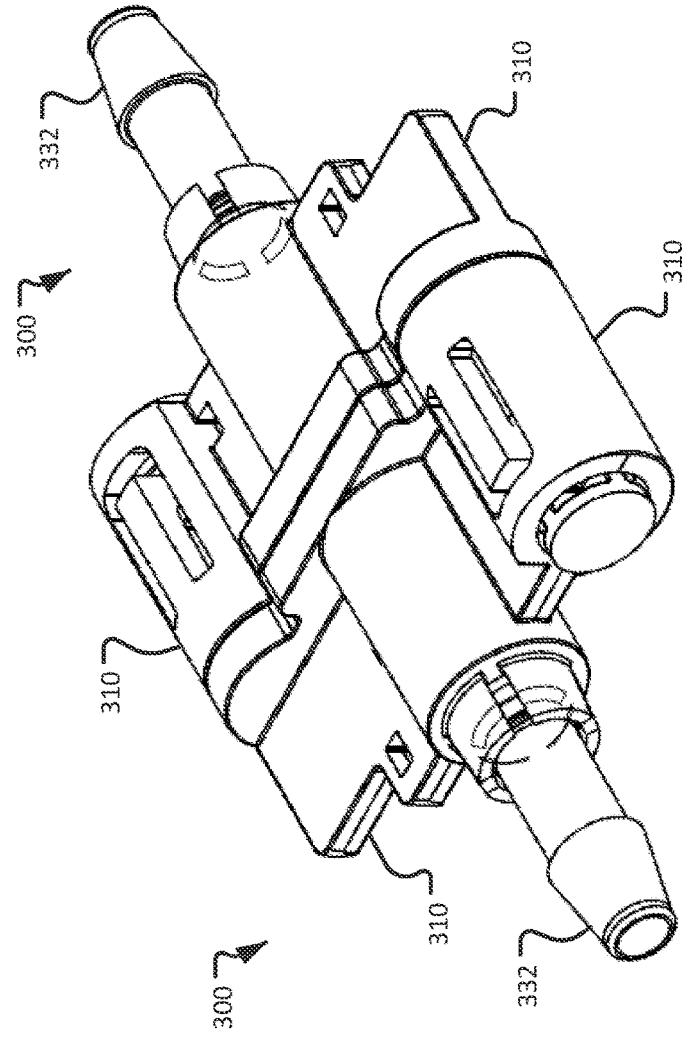
FIG. 16 is a perspective view of two of the fluid couplings of FIG. 15 in a coupled configuration.
Figure 17:
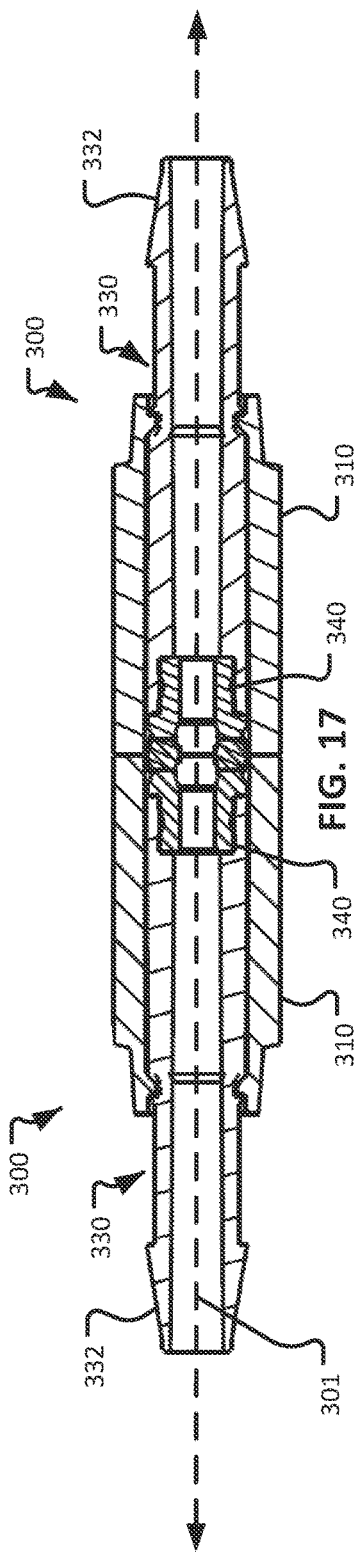
FIG. 17 is a longitudinal cross-sectional view of the two fluid couplings in the coupled configuration as shown in FIG. 16.
Figure 18:
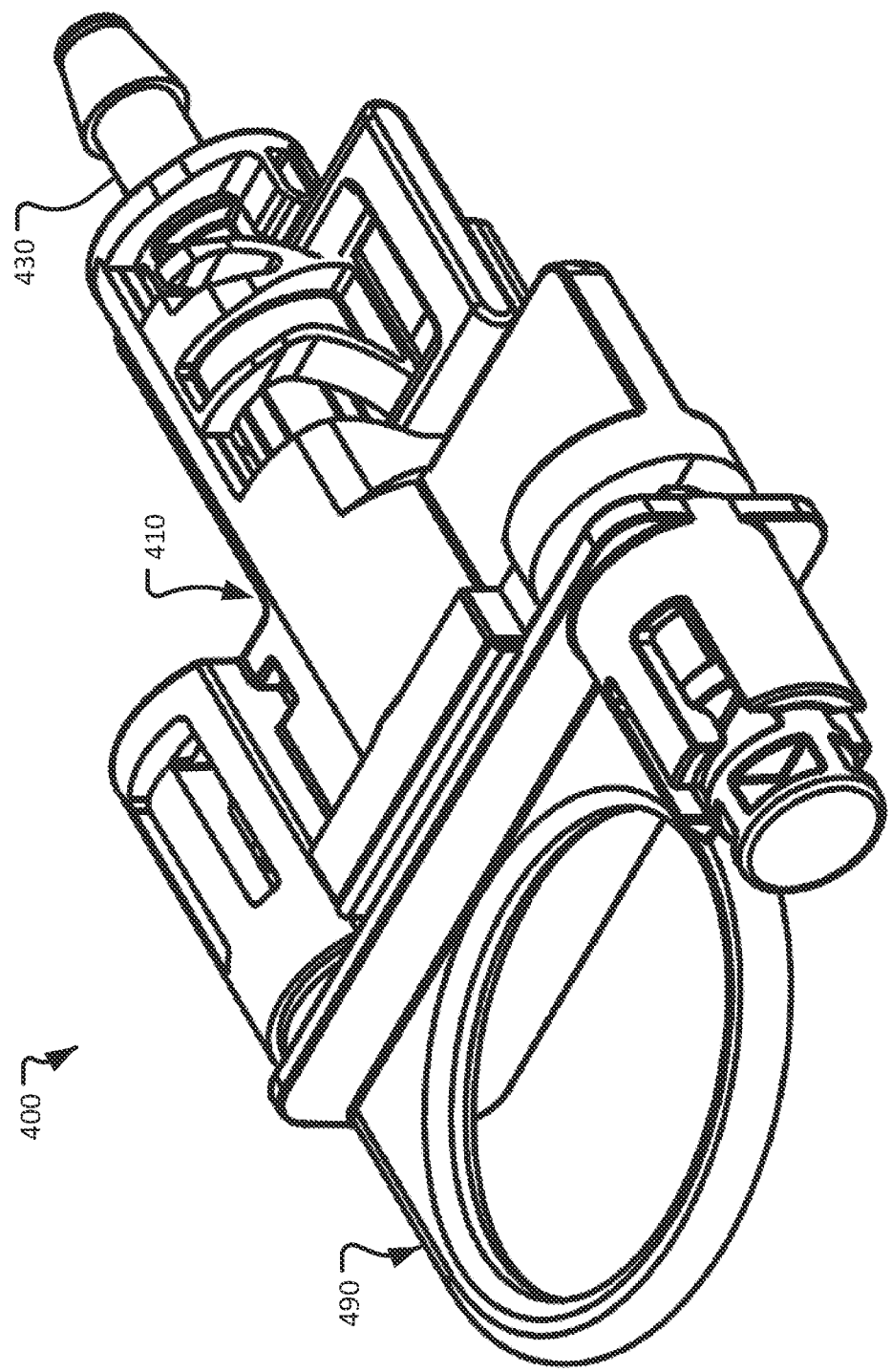
FIG. 18 is a perspective view of another example fluid coupling in accordance with some embodiments provided herein.
Figure 19:
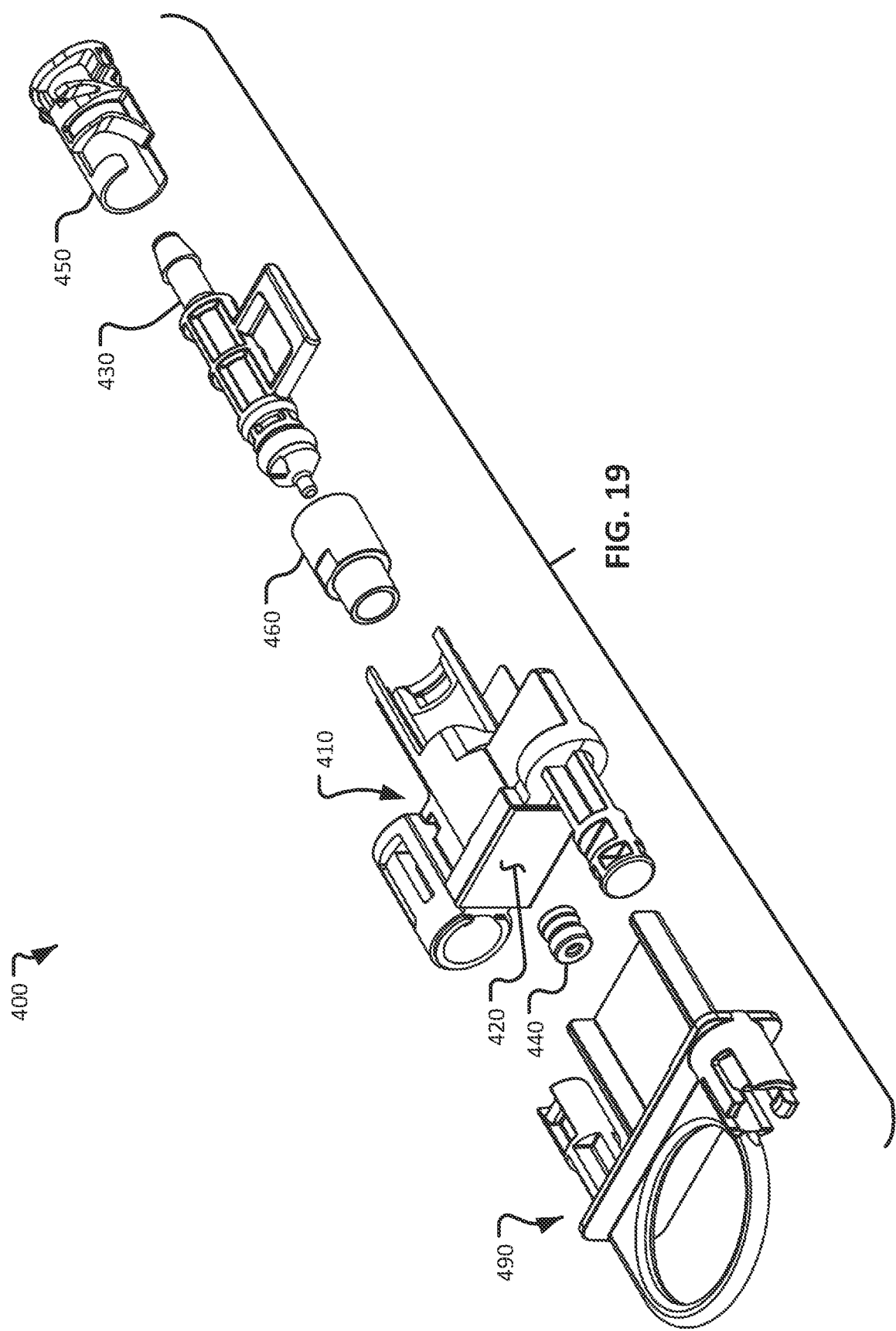
FIG. 19 is an exploded perspective view of a variation of the fluid coupling of FIG. 18.

With the two fluid coupling devices 300 latched together, the membranes 320 are then removed. This results in the operative configuration shown in FIG. 16. An open fluid flow path is created between the terminations 332. The open fluid flow path 301 is shown in FIG. 17.

The seal 340 in its static position relative to the main body 310 is the same as the seal 240 described above. The seal 340 protrudes slightly beyond the front face 312 of the main body. This protrusion of the seal 340 ensures that there is a slight compression fit between two seals 340 when two fluid coupling devices 300 latched together.

The seal 340 has multiple sealing features. The seal 340 seals against the main body 310 in two places. The seal 340 seals against the termination member 330 in four places (as shown in FIG. 14 relative to the seal 240). In total, the seal 340 has seven (7) sealing areas/features.

FIGS. 18-21 show another example fluid coupling device 400. The fluid coupling device 400 is, from a functional standpoint, a combination of the fluid coupling device 100 (having a manually actuatable valve) and the fluid coupling device 200' (with the protective cover 290').

Figure 20:
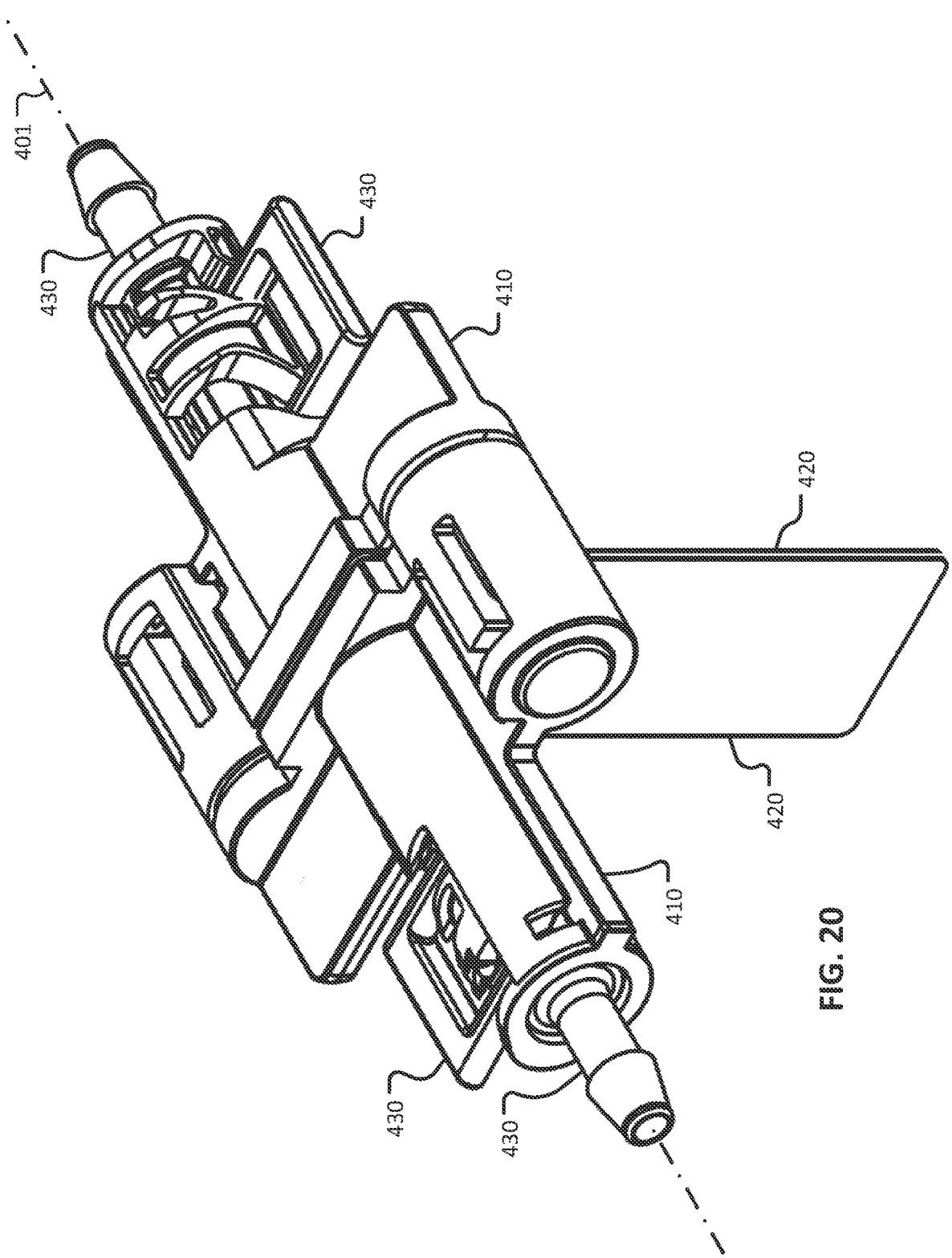
FIG. 20 is a perspective view of two of the fluid couplings of FIG. 18 in a pre-coupled configuration.
Figure 21:
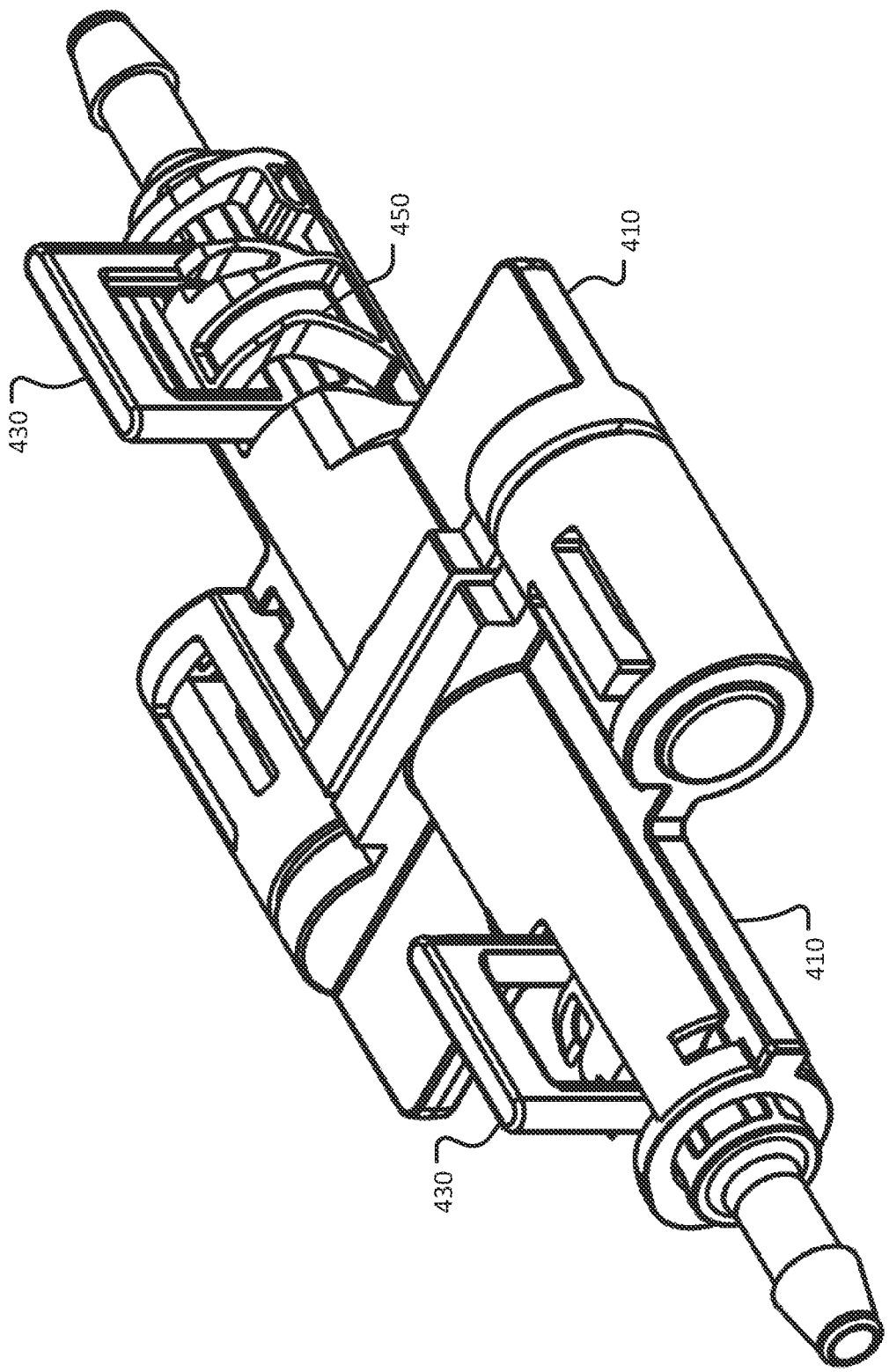
FIG. 21 is a perspective view of two of the fluid couplings of FIG. 18 in an operationally coupled configuration.

The fluid coupling device 400 includes a main body 410, a removable membrane 420, a lever valve 430, a seal 440, a cap 450, a sleeve 460, and a protective cover 490. The fluid coupling device 400 defines a longitudinal axis 401 (FIG. 20). The removable membrane 420 and the protective cover 490 are removably coupled with the main body 410. The seal 440 is coupled to the main body 410 and a portion of the seal 440 protrudes from the front face of the main body 410.

FIG. 20 shows two of the fluid coupling devices 400 in a pre-coupled configuration. With the protective covers 490 of two of the fluid coupling devices 400 removed, the two fluid coupling devices 400 can then be engaged to each other (with the membranes 420 being pushed against each other between the front faces of the main bodies 410). The two fluid coupling devices 400 will snap together and latch to each other. The action of snapping two fluid coupling devices 400 can advantageously be accompanied by audible and tactile feedback. Each fluid coupling device 400 includes a post and a post receptacle. To couple two fluid coupling devices 400 together (e.g., to snap them into engagement with each other), the post of a first fluid coupling device 400 is inserted in the post receptacle of a second fluid coupling device 400, and the post of a second fluid coupling device 400 is inserted in the post receptacle of a first fluid coupling device 400. The posts latch inside of the post receptacles.

With the fluid coupling devices 400 in the pre-coupled configuration as shown in FIG. 20, the membranes 420 can then be pulled away from the main bodies 410. When the membranes 420 are removed from between the seals 440, the seals 440 then abut each other with compression. After the removal of the membranes 420, the lever valves 430 can be manually pivoted relative to the main bodies 410 to arrive at the configuration shown in FIG. 21. In this configuration, the valves are open and a fluid flow pathway is opened through the two fluid coupling devices 400.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

What is claimed is:

1. A fluid coupling device comprising:
a main body defining a fluid flow path extending along a longitudinal axis, the main body comprising:
a front face,
a first projection extending in a direction of the longitudinal axis, and
a first projection receptacle;
a seal coupled to the main body between the first projection and the first projection receptacle and around the longitudinal axis, a portion of the seal protruding from the front face of the main body;
a removable membrane releasably attached to the front face of the main body and covering the portion of the seal protruding from the front face of the main body; and
a protective cover removably engaged with the main body and comprising: (i) a second projection receptacle releasably engaged with the first projection of the main body and (ii) a second projection releasably engaged with the first projection receptacle of the main body,
wherein the protective cover is: (i) structured without a fluid flow path and (ii) required to be removed from engagement with the main body to allow the fluid coupling device to be operatively mated with another fluid handling device.

2. The fluid coupling device of claim 1, wherein the seal comprises a circular projection that has a triangular cross-sectional shape, and wherein the circular projection extends parallel to the longitudinal axis.

3. The fluid coupling device of claim 1, wherein the seal comprises two annular concavities defined by the outer surface of the seal.

4. The fluid coupling device of claim 1, wherein the seal includes a portion having an hourglass cross-sectional shape.

5. The fluid coupling device of claim 1, wherein the fluid coupling device is genderless such that two of the fluid coupling devices can be coupled to each other.

6. The fluid coupling device of claim 1, wherein the protective cover includes a pull ring.

7. The fluid coupling device of claim 6, wherein the pull ring defines an opening configured to receive a finger.

8. The fluid coupling device of claim 7, wherein the protective cover includes a membrane receiver portion that holds and protects a portion of the removable membrane.

9. The fluid coupling device of claim 1, wherein the protective cover includes a membrane receiver portion that holds and protects a portion of the removable membrane.

* * * * *